(12) United States Patent
Varner et al.

(10) Patent No.: US 8,096,972 B2
(45) Date of Patent: Jan. 17, 2012

(54) DEVICES FOR INTRAOCULAR DRUG DELIVERY

(75) Inventors: Sign Erickson Varner, Los Angeles, CA (US); Eugene Dejuan, Jr., La Canada, CA (US); Terry Shelley, Hampstead, MD (US); Aaron Christopher Barnes, Oak Park, CA (US); Mark Humayun, La Canada, CA (US)

(73) Assignee: Johns Hopkins University, Baltimore, MD (US)

( * ) Notice: Subject to any disclaimer, the term of this patent is extended or adjusted under 35 U.S.C. 154(b) by 354 days.

(21) Appl. No.: 10/740,698

(22) Filed: Dec. 19, 2003

(65) Prior Publication Data
US 2004/0133155 A1 Jul. 8, 2004

Related U.S. Application Data

(63) Continuation of application No. 09/888,092, filed on Jun. 22, 2001, now Pat. No. 6,719,750.

(60) Provisional application No. 60/228,934, filed on Aug. 30, 2000.

(51) Int. Cl.
*A61M 31/00* (2006.01)
(52) U.S. Cl. .............. 604/93.01; 604/890.01; 604/891.1; 604/521
(58) Field of Classification Search ............... 604/890.1, 604/891.1, 93.01, 521, 174, 175; 424/427–428, 424/422
See application file for complete search history.

(56) References Cited

U.S. PATENT DOCUMENTS

| 273,410 | A | 3/1883 | Wadleigh |
|---|---|---|---|
| 3,416,530 | A | 12/1968 | Ness |
| 4,069,307 | A | 1/1978 | Higuchi et al. |
| 4,144,317 | A | 3/1979 | Higuchi et al. |
| 4,300,557 | A | 11/1981 | Refojo et al. |
| 4,304,765 | A | 12/1981 | Shell et al. |
| 4,764,377 | A | 8/1988 | Goodson |
| 4,853,224 | A | 8/1989 | Wong |
| 4,892,736 | A | 1/1990 | Goodson |
| 5,098,443 | A | 3/1992 | Parel et al. |
| 5,164,188 | A | 11/1992 | Wong |

(Continued)

FOREIGN PATENT DOCUMENTS

EA 0734721 3/1996

(Continued)

OTHER PUBLICATIONS

Berger et al., "Intravitreal Sustained Release Corticosteroid-5-Fluoruracil Conjugate in the Treatment of Experimental Proliferative Vitreoretinopathy," *Investigative Opthalmology & Visual Science*, vol. 37, No. 2, pp. 2318-2325 (Oct. 1996).

(Continued)

*Primary Examiner* — Bhisma Mehta
(74) *Attorney, Agent, or Firm* — Kagan Binder, PLLC

(57) ABSTRACT

A therapeutic agent delivery device that is particularly suitable for delivery of a therapeutic agent to limited access regions, such as the posterior chamber of the eye and inner ear. Preferred devices of the invention are minimally invasive, refillable and may be easily fixed to the treatment area. Preferred delivery devices of the invention also include those that comprise a non-linear shaped body member housing one or more substances and a delivery mechanism for the sustained delivery of the one or more substances from the non-linear shaped body member to the patient.

68 Claims, 9 Drawing Sheets

U.S. PATENT DOCUMENTS

| | | | |
|---|---|---|---|
| 5,246,867 A | | 9/1993 | Lakowicz et al. |
| 5,300,114 A | | 4/1994 | Gwon et al. |
| 5,372,577 A | | 12/1994 | Ungerleider |
| 5,378,475 A | | 1/1995 | Smith et al. |
| 5,395,618 A | * | 3/1995 | Darougar et al. ............ 424/427 |
| 5,443,505 A | | 8/1995 | Wong et al. |
| 5,466,233 A | * | 11/1995 | Weiner et al. ............ 604/890.1 |
| 5,472,436 A | | 12/1995 | Fremstad |
| 5,476,511 A | | 12/1995 | Gwon et al. |
| 5,501,856 A | | 3/1996 | Ohtori et al. |
| 5,551,427 A | * | 9/1996 | Altman ......................... 600/374 |
| 5,578,075 A | | 11/1996 | Dayton |
| 5,582,616 A | | 12/1996 | Bolduc et al. ................. 606/143 |
| 5,679,400 A | | 10/1997 | Tuch |
| 5,725,493 A | | 3/1998 | Avery et al. |
| 5,766,242 A | | 6/1998 | Wong et al. |
| 5,773,019 A | | 6/1998 | Ashton et al. |
| 5,824,072 A | | 10/1998 | Wong ............................... 623/4 |
| 5,830,173 A | | 11/1998 | Avery et al. |
| 5,868,697 A | * | 2/1999 | Richter et al. ..................... 604/8 |
| 5,904,144 A | | 5/1999 | Hammang et al. |
| 5,928,662 A | | 7/1999 | Philips |
| 5,972,027 A | * | 10/1999 | Johnson ....................... 623/1.42 |
| 5,972,369 A | | 10/1999 | Roorda et al. |
| 5,989,579 A | | 11/1999 | Darougar et al. |
| 6,074,661 A | | 6/2000 | Olejnik et al. |
| 6,153,252 A | | 11/2000 | Hossainy et al. |
| 6,177,095 B1 | | 1/2001 | Sawhney et al. |
| 6,187,370 B1 | | 2/2001 | Dinh et al. |
| 6,214,901 B1 | | 4/2001 | Chudzik et al. |
| 6,217,895 B1 | | 4/2001 | Guo et al. |
| 6,251,090 B1 | | 6/2001 | Avery et al. |
| 6,306,125 B1 | | 10/2001 | Parker et al. |
| 6,331,313 B1 | | 12/2001 | Wong et al. |
| 6,344,035 B1 | | 2/2002 | Chudzik et al. |
| 6,375,972 B1 | | 4/2002 | Guo et al. |
| 6,399,144 B2 | | 6/2002 | Dinh et al. |
| 6,399,655 B1 | | 6/2002 | de Juan, Jr. |
| 6,478,776 B1 | * | 11/2002 | Rosenman et al. ....... 604/164.01 |
| 6,548,078 B2 | | 4/2003 | Guo et al. |
| 6,713,081 B2 | | 3/2004 | Robinson et al. |
| 6,719,750 B2 | | 4/2004 | Varner et al. |
| 2002/0013605 A1 | | 1/2002 | Bolduc et al. |
| 2002/0026176 A1 | | 2/2002 | Varner et al. |
| 2002/0032434 A1 | | 3/2002 | Chudzik et al. |
| 2002/0114823 A1 | | 8/2002 | Sirhan et al. |
| 2002/0165265 A1 | | 11/2002 | Hunter et al. |
| 2002/0168394 A1 | | 11/2002 | Hossainy et al. |
| 2002/0188037 A1 | | 12/2002 | Chudzik et al. |
| 2002/0198511 A1 | | 12/2002 | Varner et al. |
| 2003/0014036 A1 | | 1/2003 | Varner et al. |
| 2003/0021828 A1 | | 1/2003 | Guo et al. |
| 2003/0031780 A1 | | 2/2003 | Chudzik et al. |
| 2003/0158598 A1 | | 8/2003 | Ashton et al. |
| 2004/0022853 A1 | | 2/2004 | Ashton et al. |
| 2004/0047911 A1 | | 3/2004 | Lyu et al. |
| 2004/0121014 A1 | | 6/2004 | Guo et al. |

FOREIGN PATENT DOCUMENTS

| | | |
|---|---|---|
| EA | 0832655 | 6/1997 |
| EP | 0623354 | 4/1994 |
| EP | 0879595 | 4/1998 |
| EP | 0923953 | 6/1998 |
| WO | WO-89/05664 | 6/1989 |
| WO | WO 95/03036 | 2/1995 |
| WO | WO 95/28984 | 11/1995 |
| WO | WO-97/10011 | 3/1997 |
| WO | WO-97/37640 | 10/1997 |
| WO | WO-98/32474 | 7/1998 |
| WO | WO-98/58690 | 12/1998 |
| WO | WO-99/01114 | 1/1999 |
| WO | WO-99/36071 | 7/1999 |
| WO | WO-99/55396 | 11/1999 |
| WO | WO-00/02564 | 1/2000 |
| WO | WO-00/21584 | 4/2000 |
| WO | WO-01/08718 | 2/2001 |
| WO | WO-01/30323 | 5/2001 |
| WO | WO-01/32140 | 5/2001 |
| WO | WO-02/17831 | 3/2002 |
| WO | WO-02/056790 | 7/2002 |
| WO | WO-03/026718 | 4/2003 |
| WO | WO-2004/028477 | 4/2004 |

OTHER PUBLICATIONS

Berger et al., "Intravitreal Sustained Release Dexamethasone/5-FU Device in the Treatment of Experimental PVR," *Investigative Opthalmology & Visual Science*, vol. 35, No. 4, p. 1923 (Mar. 15, 1994).

Ishibashi et al, "Effects of Intravitreal Administration of Seroids on Experimental subretinal Neovascularization in the Subhuman Primate," *Arch Ophihalmol*, vol. 103, pp. 708-711 (May 1985).

Jaffee et al., "Intravitreal Sustained Release Triamcinolone/5-FU Conjugate Suspension in the Treatment of Experimental," *Investigative Ophthalmology & Visual Science*, vol. 36, No. 4, p. S161 (Mar. 15, 1995).

Zhou et al., "A Multi-Drug Controlled-Release Implant for Intraocular Treatment of Proliferative Vitreoretinopathy," *Proc. Int. Symp. Control. re. Bioact. Mater.*, vol. 24, pp. 625-626 (1997).

Zhou et al.,"Development of a multiple-drug delivery implant for intraocular management of proliferative vitreoretinopathy," *Journal of Controlled Release*, vol. 55, pp. 281-295 (1998).

Jaffee et al., "Safety and Pharmacokinetics of an Intraocular Fluocinolone Acetonide Sustained Delivery Device," *Investigative Ophthalmology & Visual Science*, vol. 41, No. 11 pp. 3569-3575 (Oct. 2000).

Varner et al., "Development of a Minimally Invasive Intravitreal Implant for Drug Delivery," *ARVO Abstracts Online*, 4 pages (May 8, 2003).

T.J. Smith et al., "Intravitreal Sustained-Release Ganciclovir," Opthalmol., vol. 110, 255-258 (1992).

G.E. Sanborn, et al., "Sustained-Release Ganciclovir Therapy for Treatment of Cytomegalovirus Retinitis. Use of an Intravitreal Device," Arch. Opthalmol., vol. 110, 188-195 (1992).

International Search Report of International Application No. PCT/US01/20119, May 7, 2002.

\* cited by examiner

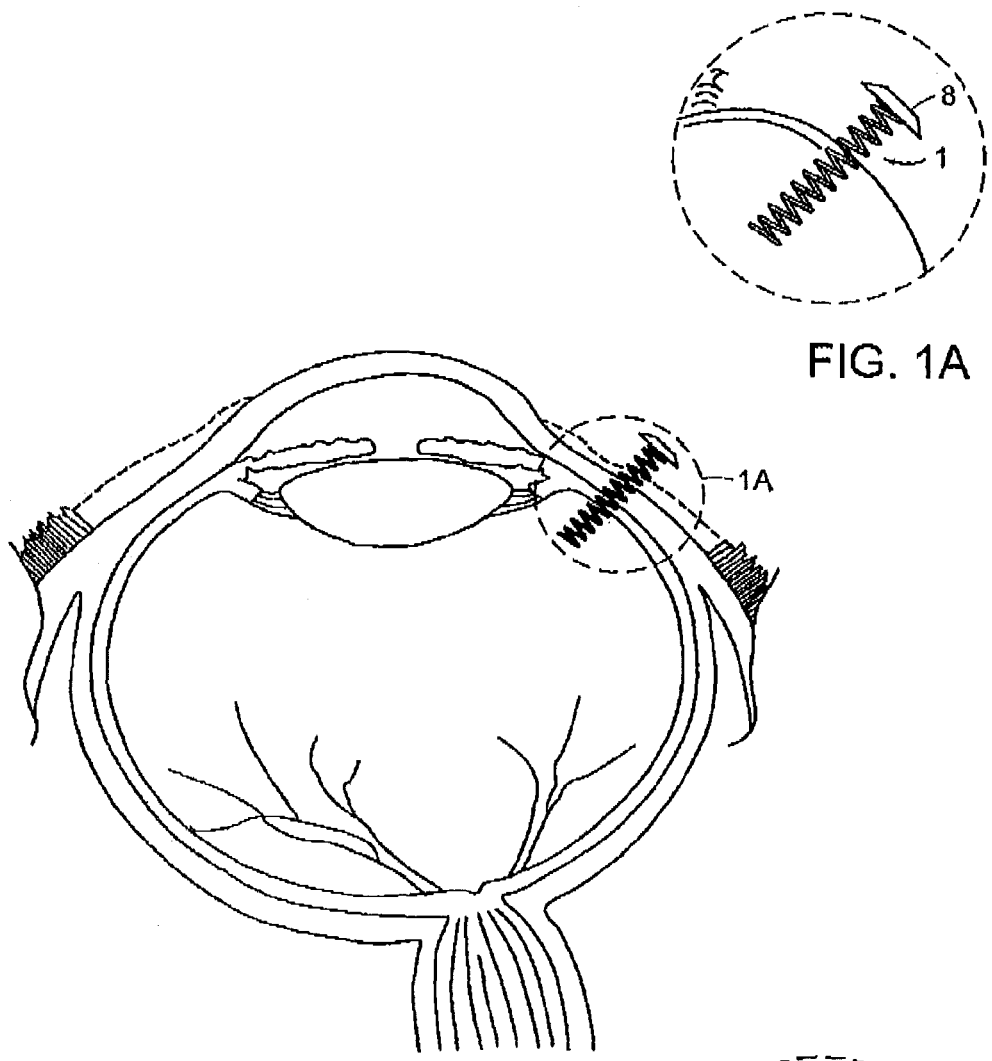
FIG. 1A
FIG. 1
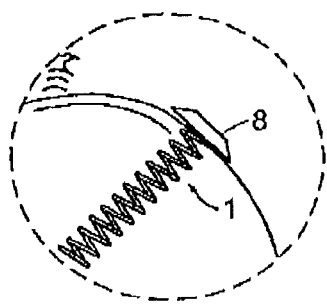
FIG. 1B

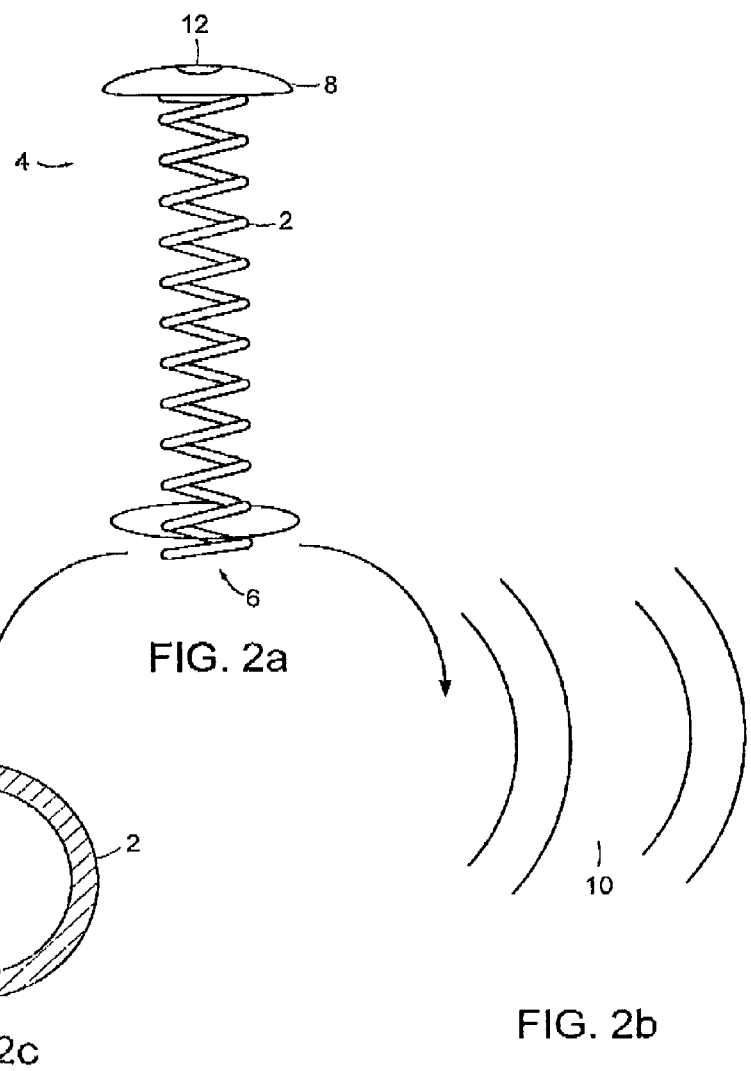

DEVICES FOR INTRAOCULAR DRUG DELIVERY

The present application claims the benefit of U.S. patent application Ser. No. 09/888,002 filed Jun. 22, 2001, now U.S. Pat. No. 6,719,750, and U.S. provisional application No. 60/228,934, flied Aug. 30, 2000, incorporated herein by reference.

FIELD OF THE INVENTION

The present invention relates to a device and method for intraocular delivery of therapeutic agents. Preferred devices of the invention include a non-linear portion that resides within a patient's eye during use that can facilitate the delivery of a therapeutic agent.

BACKGROUND

The delivery of drugs to the eye presents many challenges. The ocular absorption of systemically administered pharmacologic agents is limited by the blood ocular barrier, namely the tight junctions of the retinal pigment epithelium and vascular endothelial cells. High systemic doses can penetrate this blood ocular barrier in relatively small amounts, but expose the patient to the risk of systemic toxicity. Topical delivery of drugs often results in limited ocular absorption due to the complex hydrophobic/hydrophilic properties of the cornea and sclera. Additionally, topical agents are mechanically removed by the blink mechanism such that only approximately 15% of a single drop is absorbed. Diffusion of topically administered drugs to the posterior chamber occurs, but often at sub-therapeutic levels. Intravitreal injection of drugs is an effective means of delivering a drug to the posterior segment in high concentrations. However, these repeated intraocular injections carry the risk of infection, hemorrhage and retinal detachment. Patients also find this procedure somewhat difficult to endure.

Local sustained delivery of therapeutics to the posterior chamber is critical in managing several chronic diseases of the eye. To address this need, several drug delivery devices have been developed for intraocular insertion into the vitreous region of the eye.

U.S. Pat. No. 4,300,557, for example, describes an intraocular implant in the form of a silicone capsule, which can be filled with a drug to be delivered. The implant is inserted through an incision into the vitreous region of the eye. After insertion of the implant, the incision is closed and the capsule remains in place for a period of time. Attached to the implant is a tube that passes through the surface of the eye. The tube may be used for subsequent injection of a drug while the implant is in the eye. The implant may be removed by making a second surgical incision into the eye and retrieving the implant. While in the vitreous, the device is not anchored and may move about freely. Because the overall shape of the capsule is linear, the amount of drug that may held by the device and that may be delivered over the surface area of the device is limited. If the width of the capsule is increased, excessive sized incisions will be required for insertion of the device. If the length of the capsule is increased to greater than 1 cm, the implant will pass into the central visual field of the eye, thereby causing blind spots in the patient's eye as well as increase risk of damage to the retinal tissue and lens capsule.

U.S. Pat. No. 5,378,475 describes a device which has been developed for insertion in the vitreous region of the eye, and is described in T. J. Smith et al., Sustained-Release Ganciclovir, *Arch. Ophthalmol*, 110, 255-258 (1992) and G. E. Sanbom, et al., Sustained-Release Ganciclovir Therapy for Treatment of Cytomegalovirus Retinitis. Use of an Intravitreal Device, *Arch. Ophthalmol*, 110, 188-195 (1992). This device consists of an inner core of pharmacologic agent surrounded by two coatings with different permeabilities. Drug diffuses through a small opening in one of these coatings achieving near-order release kinetics. It is implanted in the region of the pars plana through a 3.5-5.0 mm scleral incision. The implant must be removed and replaced every 6 months in the operating room as the drug becomes depleted. There is an approximately 25% complication rate from these procedures. The device is membrane diffusion drug delivery system that relies on EVA/PVA polymers to mediate release rate. Thus, many agents cannot be effectively delivered from such a system because their permeation rate through the rate controlling material of the system is too small to produce a useful effect. Other agents cannot be satisfactorily delivered by diffusional devices because of a particular chemical characteristic of the agent. This includes salts, because of their ionic character, and unstable polar compounds that cannot be formulated into a composition suitable for storage and delivery from such systems.

U.S. Pat. No. 5,098,443 describes certain specific implants that are inserted through incisions made in the eye wall or sutured around the globe of the eye. These rings may be formed from biodegradable polymers containing microparticles of drug. Alternatively, the implant may be in the form of a hollow flexible polymeric cocoon with the drug disposed therewithin for slow release by osmosis. No anchoring device is described.

U.S. Pat. No. 5,466,233 describes a certain tack for intraocular drug delivery. This device has an end that is positioned in the vitreous cavity while the head remains external to the eye and abuts the scleral surface. The tack contains a fixation portion to attempt to retain attachment within the eye. Because the overall shape of the capsule is linear, the amount of drug that may held by the device and the surface area through which the drug may be delivered is limited. If the width of the capsule is increased, excessive sized incisions will be required for insertion of the device. If the length of the capsule is increased to greater than 1 cm, the implant will pass into the central visual field of the eye, thereby causing blind spots in the patient's eyes well as increase risk of damage to the retinal tissue and lens capsule.

SUMMARY OF THE INVENTION

The present invention provides methods and devices for the intraocular delivery of substances including, for example, therapeutic agents and medicaments.

Preferred devices of the invention have a non-linear shape during residence within a patient's eye. Preferred designs have multiple turns or angles, particularly substantially coil or helical configurations, at least for those portions that reside within a patient's eye during use.

Preferred device of the invention also include those that have a quite small cross-section shape, at least with respect to areas that reside within a patient's eye during use. Such devices can be implanted by minimally invasive surgical procedures, including without the need for any sutures to implant or after use of the use.

An exemplary embodiment of the delivery device includes a body member that is non-linear in shape. In one embodiment, the device has a non-linear shape before, during and after the device is inserted into the eye. In another embodiment, the device is fabricated of a "shape memory" material wherein the device is linear as it is inserted into the eye and wherein the device takes on a non-linear shape once it is implanted in the eye. Preferred shape memory materials include known materials such as, for example, shape memory alloys (SMA) like nitinol, shape memory polymers (SMP) like AB-polymer networks based on oligo(e-caprolactone) dimethacrylates and n-butyl acrylate.

We have found the non-linear shape of the body member provides a number of advantages. The non-linear shape provides a built-in anchoring mechanism that prevents unwanted movement of the device and unwanted ejection of the device out of the eye since the non-linear shape of the body member requires manipulation of the device to get it out of an incision. For example, in a preferred embodiment, wherein the implant is in the shape of a coil, the device can be removed only by twisting the device out of the eye and, thus, is not susceptible to ejection by the eye or unwanted movement within the eye. Further, the non-linear shape geometry of the body member provides greater surface area per length of the device. This is advantageous because it is desirable to limit the length of drug delivery implants to prevent the implant from entering the central visual field (See FIG. 6 which follows). If the implant enters the central visual field, this will result in blind spots in the patient's vision and will increase the risk of damage to the retina tissue and lens capsule. By forming the body member in a non-linear shape, the device of the present invention holds a greater volume of materials per length of the device and it also provides a larger surface area per length of the device through which the material may be delivered.

The delivery device may further include a rim or cap at its proximal end. During use, the device is inserted into the eye through an incision until the rim or cap abuts the incision. If desired, the rim or cap may then be sutured to the eye to further stabilize and prevent the device from moving once it is implanted in its desired location.

In one embodiment, body member has a lumen extending along its length for housing the substance to be delivered. Preferably, a port in fluid communication with the lumen is located at the proximal end of the device. This allows for filling and refilling of the device after the device has been implanted in the eye. The substance in the lumen can then be delivered to the eye by a delivery mechanism. The lumen, in some embodiments, may further include a number of dividers to form a plurality of compartments each of which could be filled with a different substance, thereby allowing for delivery of more that one substances by the same device at the same time, if desired.

In one embodiment, the delivery mechanism comprises one or more exit apertures located at the distal end of the body member. In another embodiment, the delivery mechanism comprises a plurality of openings along the body member. In another embodiment, the delivery mechanism comprises the material forming the body member. For example, the material forming the body member may be a material that is permeable or semi-permeable to the substance to be delivered. In another embodiment, the body member is fabricated of a synthetic biodegradable polymer containing microparticles of the substance to be delivered. As the polymer decomposes, the substance to be delivered is released into the eye.

Other aspects and embodiments of the invention are discussed infra.

BRIEF DESCRIPTION OF THE DRAWINGS

FIG. 1A shows a magnified view of the delivery device outlined in FIG. 1. FIG. 1B shows a magnified view of the delivery device outlined in FIG. 1 and inserted into the eye through an incision until the rim or cap abuts the incision.

FIG. 2a illustrates the delivery device in accordance with one embodiment of the present invention.

FIG. 2b is an enlarged view of a portion of the body member of the delivery device shown in FIG. 2a showing the lumen.

FIG. 2c is an enlarged cross-sectional view of the body member of the delivery device shown in FIG. 2a.

FIG. 4b-1 illustrates the ports associated with the plurality of lumens shown in FIG. 4a FIG. 4c is an exploded view of the cap or rim and a portion of the body member shown in FIG. 4a showing another arrangement of a plurality of lumens. FIG. 4c-1 illustrates the ports associated with the plurality of lumens shown in FIG. 4c.

FIG. 4d-1 is a magnified view of the outlined segment of the body member shown in FIG. 4d-2. FIG. 4d-2 illustrates a body member comprising a cluster of tubes.

DETAILED DESCRIPTION OF THE INVENTION

Figure 3A:
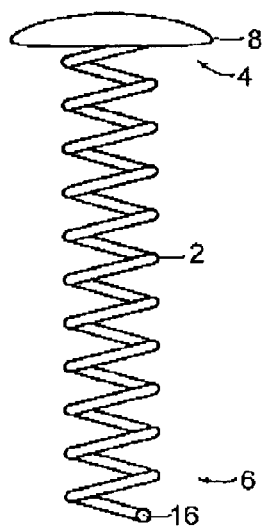
FIG. 3a illustrates the delivery device having a delivery mechanism in accordance with one embodiment of the present invention.

As discussed above, preferred delivery devices of the invention have a non-linear (arcuate) shape during residence within a patient's eye. Preferred designs have multiple turns or angles. For example, preferred designs the device has at least two, three, four, five, six, seven, right, nine or ten separate deviations from a linear path. A coil design is particularly preferred, although other multiple-angle configurations are also suitable such as a substantially Z-shape and the like.

Referring now to the various figures of the drawing, wherein like reference characters refer to like parts, there is shown various views of a delivery device 1, in accordance with the invention.

As shown in FIGS. 1-5c, the delivery device 1 includes a non-linear shaped body member 2 having a proximal end 4, a distal end 6. In one preferred embodiment, the body member 2 has a coil shape, as shown in FIGS. 1-5c. However, the shape of the body member 2 is not limited to a coil shape and other non-linear shapes may be used such as, for example, other random curled shapes, a zig-zag shape, a "J" shape and the like. For at least some aspects of the invention, a substantially "C" shape configuration is less preferred.

As discussed above, the non-linear shape of the body member 2 provides a number of advantages. The large intravitreal surface area provided by the non-linear shape geometry of the body member 2, which is implanted in the eye and is in contact with the vitreous fluid, can allow for more optimal sustained release of the substance through diffusion, enzymatic degradation, active pumping and other types of delivery. When implanted in the eye, it is desirable to limit the length "L" of drug delivery implants to prevent the drug delivery implant from entering the central visual field "A" (See FIG. 6). If the implant enters the central visual field A, this will result in blind spots in the patient's vision and will increase the risk of damage to the retina tissue and lens capsule. Thus, for example, when the implant is inserted at the pars plana, the distance from the implantation site on the pars plana to the central visual field is approximately 1 cm. Thus, the overall length of the implant is preferably less than 1 cm. By providing a body member 2 that has a non-linear shape, the device of the present invention holds a greater volume of materials per length of the device without having to make the cross section of the device and, thus, the size of the insertion incision) larger, and it also provides a larger surface area per length of the device through which the material may be delivered. Still further, the non-linear shape of the body member 2 provides a built-in anchoring system that prevents unwanted movement of the device and unwanted ejection of the device out of the eye since the non-linear shape of the body member requires manipulation of the device to get it out of an incision (e.g. a coil-shaped body member 2 would require twisting the device out of the eye, and a zig-zag shaped body member 2 would require moving the device back and forth to remove the device from the eye).

In one preferred embodiment, the delivery device has a coil-shaped body member 2 as shown in FIGS. 1-5c. The coil shape of the device provides a large intravitreal surface area through which material can be delivered. Further, the coil shape of the body member allows the device to be screwed or twisted into the eye through an incision approximately the same size as the outer diameter of the tube forming the body member 2. This would be similarly applicable for other described shapes such as, for example, zig-zag shapes. "J" shapes, and "C" shapes which would, likewise, be similarly manipulated into the eye through an incision approximately the same size as the outer diameter of the tube forming the thus shaped body member 2. As such, the device is insertable or implantable within the eye through an incision smaller than the cross-section of the coil-shaped (and, likewise, zig-zag, "J", and "C" shaped) body member. Still further, the coil shape of the body member acts as an anchoring mechanism that holds the delivery device 1 within the eye and prevents unwanted movement of the delivery device and unwanted ejection of the delivery device 1 out of the eye. Due to the coil shape, the delivery device 1 must be twisted and unscrewed out of the eye.

In general, the materials used in fabricating the body member 2 are not particularly limited, provided these materials are biocompatible. Preferably, these materials are also insoluble in the body fluids and tissues that the device comes into contact with. It is further preferred that the body member 2 is fabricated of a flexible material so that small movements of the delivery device will not be translated to the retina, thereby minimizing the risk of retinal tearing, detachment and other damage. In some embodiments, as described in further detail below, it is preferable that at least the distal end 6 of body member 2 is fabricated of a rigid, non-pliable material. In some embodiments, as described in further detail below, it is preferable that at least a portion of the material used to form the body member 2 is permeable or semi-permeable to the substance to be delivered. In some embodiments, as set out above, it is preferable that the body member is fabricated of a material having shape memory and/or superelastic characteristics.

In one embodiment, the body member 2 is fabricated of a nonbiodegradable polymer. Such nonbiodegradable polymers are well-known and may include, for example, polymethylmethacrylate, a silicone elastomer, or silicone rubber. Other suitable non-erodible, biocompatible polymers which may be used in fabricating the body member 2 may include polyolefins such as polypropylene and polyethylene, homopolymers, and copolymers of vinyl acetate such as ethylene vinyl acetate copolymer, polyvinylchlorides, homopolymers and copolymers of acrylates such as polyethylmethacrylate, polyurethanes, polyvinylpyrrolidone, 2-pyrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, natural rubber, polyisobutylene, polymethylstyrene and other similar non-erodible biocompatible polymers.

The body member 2 of the delivery device 1 can, in one embodiment, have a non-linear shape prior to, during and after insertion of the device into the eye. Alternatively, the delivery device 1 can be fabricated of a material having shape memory and/or superelastic characteristics that allows the device to be deformed and made, for example, linear, for easier insertion into the eye and which returns to its original shape after it is inserted into the eye. In this embodiment, the delivery device 1 has a "memory shape" that it will take on under certain conditions. For example, the delivery device 1 may have a zig-zag or coiled memory shape. Then, when the surgeon wishes to implant the device into the eye, the surgeon may deform the delivery device 1 into a linear shape for quick and easy insertion of the device through an incision the size of the cross section of the linear shaped device. Upon insertion of the delivery device 1, the device can then take on its zig-zag, coiled or other memory shape.

Materials having shape memory and/or superelastic characteristics are well-known and may include any materials known in the art such as, for example, shape memory alloys (SMA) like nitinol (Ni—Ti alloy) and shape memory polymers (SMP) like AB-polymer networks based on oligo(e-caprolactone) dimethacrylates and n-butyl acrylate. Shape memory alloys generally have at least two phases: (1) a martensite phase, which has a relatively low tensile strength and which is stable at relatively low temperatures, and (2) an austenite phase, which has a relatively high tensile strength and which is stable at temperatures higher than the martensite phase. The shape memory characteristics are imparted on the material by heating the material to a temperature above the temperature at which the austenite phase is stable. While the material is heated to this temperature, the device is held in the "memory shape", which is shape that is desired to be "remembered". Such materials and methods of imparting shape memory characteristics are further described in, for example, U.S. Pat. No. 4,665,905, U.S. Pat. No. 4,925,445 and U.S. Pat. No. 6,245,100.

Preferably, the delivery device of the present invention takes advantage of the superelastic properties of the material to extend the device into a linear shape. Once injected into the eye in an unconstrained form, the device will retain its memory shape.

The distal end 6 of the body member 2 may be blunt or, in some embodiments, it is pointed or has a beveled ramp-like configuration so that the distal end 6 may be used to pierce the eye during insertion. In one embodiment, the distal end 6 has a ramp-like angle of about 30°. If the distal end 6 of the body member 2 is used to pierce the eye during insertion, at least the distal end 6 is fabricated of a rigid, non-pliable material suitable for piercing the eye. Such materials are well known and may include, for example, polyimide and similar materials.

As shown in FIGS. 1, 2a, 3a-c and 5a-c, a rim or cap 8 may further be located at the proximal end 4 of the body member 2 to assist in stabilizing the device 1 once implanted in the eye. Preferably, the delivery device 1 is inserted into the eye through an incision until the rim or cap 8 abuts the incision. If desired, the rim or cap 8 may then be sutured to the eye to further stabilize and prevent the device from moving once it is implanted in its desired location.

The overall size and shape of the rim or cap 8 is not particularly limited provided that irritation to the eye is limited. For example, while the rim or cap 8 is shown circular in shape, the rim or cap may be of any shape, for example, circular, rectangular, triangular, etc. However, to minimize irritation to the eye, the rim or cap 8 preferably has rounded edges. Further, the rim or cap 8 is designed such that it remains outside the eye and, as such, the rim or cap 8 is sized so that it will not pass into the eye through the opening in the eye through which the device is inserted. In some embodiments, the cap 8 is sized to provide a cross-section larger than the cross-section area of the coil or the zig-zag shape or the cross-section of the coil-shaped member, for example, as shown in FIGS. 1a, 2a, 3a-c, and 5a-b. The rim or cap 8 may further be designed such that it can be easily sutured or otherwise secured to the surface surrounding the opening in the eye and may, for example, contain a plurality of holes (not shown) through which sutures may pass.

The materials used in fabricating the rim or cap 8 are not particularly limited, provided these materials are biocompatible and preferably insoluble in the body fluids and tissues that the device comes into contact with. Further, it is preferred that the rim or cap 8 is fabricated of a material that does not cause irritation to the portion of the eye that it contacts. As such, preferred materials are pliable and may include, by way of example, various polymers including, for example, silicone elastomers and rubbers, polyolefins, polyurethanes, acrylates, polycarbonates, polyamides, polyimides, polyesters, and polysulfones.

In one embodiment, as shown in FIGS. 2a-4c and 5a-5c, the non-linear body member 2 is fabricated of a tube that is wound into a coiled shape. As shown in the Figures, the tube forming the non-linear body member 2 is preferably cylindrical in shape, with a circular cross-section. However, the shape of the tube is not limited and, for example, may alternatively have square, rectangular, octagonal or other cross-sectional shapes. Preferably, the tube has a lumen 10 extending along its length for housing the substance to be delivered. In one embodiment, the lumen 10 is filled with the substance prior to inserting the device into the eye. Alternatively, the lumen 10 may be filled with the substance after the delivery device has been inserted into the eye. This may be accomplished by providing a port 12 near the proximal end 4 of the body member 2 in fluid communication with the lumen 10. This further allows for refilling of the device during use, if required.

In one embodiment, the port 12 is preferably designed such that the needle of a syringe, or similar injection mechanism, may be inserted into the port 12 and the substance injected by the syringe or injection mechanism. Thus, the substance travels through the port 12 and into the lumen 10. The port 12 preferably forms a snug seal about the needle of the syringe or injection mechanism to prevent leakage of the substance out of the port 12 around the syringe needle or injection mechanism and to provide sterile injection of agent into the lumen 10. If desired, fittings or collars (not shown), through which a syringe needle or injection mechanism may be inserted and which form a snug seal about the syringe needle or injection mechanism, may be mounted on the port 12. Upon injection of the substance into the delivery device, the needle of the syringe or the injection mechanism is removed from the port 12 and the port 12 sealed. This may be accomplished by providing a removable cover (not shown) on the port 12 that may be removed for injection of the substance and replaced when the substance has been injected. In a preferred embodiment, the port 12 is fabricated of an injectable self-sealing material through which the needle or injection mechanism may be inserted and which seals off automatically when the needle or injection mechanism is removed. Such materials are known and include, for example, silicone rubber, silicone elastomers and polyolefin.

Once the device is implanted in the desired location and the substance is housed within the lumen 10, the substance can then be delivered to the eye by a delivery mechanism.

Figure 3B:
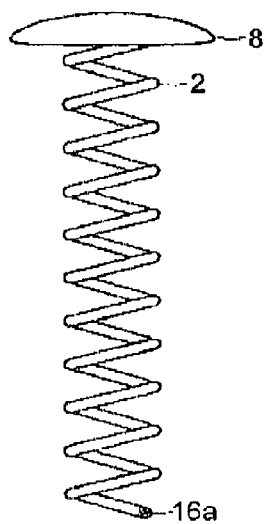
FIG. 3b illustrates the delivery device having a delivery mechanism in accordance with another embodiment of the present invention.

In one embodiment, as shown in FIG. 3a, the delivery mechanism comprises an exit aperture 16 located at the distal end 6 of the body member 2. Alternatively, as shown in FIG. 3b, a plurality of exit apertures 16a located at the distal end 6 of the body member 2 may form the delivery mechanism. The number and size of the one or more exit apertures 16 may vary depending on the desired rate of delivery of the agent and may be readily determined by one of skill in the art. The one or more exit apertures 16 are designed such that the substance is slowly diffused rather than expelled as a fluid stream, which may damage the delicate tissues of the eye. For example, in one embodiment, this may be achieved by, for example, placing a covering or lining (not shown) over the distal exit aperture 16, wherein the covering or lining has a particular porosity to the agent or wherein the covering or lining is fabricated of a diffusion or rate-limiting membrane, matrix material or similar material.

Figure 3C:
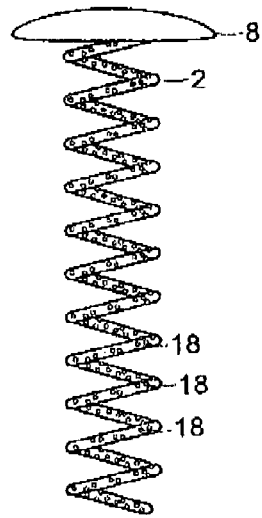
FIG. 3c illustrates the delivery device having a delivery mechanism in accordance with another embodiment of the present invention.

In another embodiment, for example, as shown in FIG. 3c, the delivery mechanism comprises a plurality of openings 18 along the body member 2. The number and size of the one or more openings 18 may vary depending on the desired rate of delivery of the agent and may be readily determined by one of skill in the art. Further, the location of the plurality of openings 18 may be situated so as to deliver the substance at a particular location once the device is implanted in the eye. The plurality of openings 18 are designed such that the substance is slowly diffused rather than expelled as a fluid stream, which may damage the delicate tissues of the eye. In this embodiment, an exit aperture 16 at the distal end 6 of the body member 2 as described above may also be included.

In another embodiment, the delivery mechanism comprises the material forming the body member 2. For example, the material forming the body member 2 may be a material that is permeable or semi-permeable to the substance to be delivered. Such materials may vary depending on the particular application and the substance to be delivered and may be readily determined by one of skill in the art. By way of example, some suitable permeable materials may include polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers.

The particular material used to fabricate the body member 2 may be chosen to provide a particular rate of delivery of the substance, which may be readily determined by one of skill in the art. Further, the rate of delivery of the substance may also be increased or decreased by varying the percentage of the body member 2 formed of the material permeable to the agent. Thus, for example, to provide a slower rate of delivery, the body member 2 may be fabricated of 50% or less permeable material. For example, the body member 2 may be fabricated of 1%, 5%, 10%, 20%, 30%, 40% or 50% of permeable material. For a faster rate of delivery, the body member 2 may be fabricated of greater than 50% of permeable material. For example, the body member 2 may be fabricated of 51%, 55%, 60%, 70%, 80%, 90% or 100% of permeable material. When one or more portions of the body member 2, rather than the whole body member 2, is fabricated of a permeable or semi-permeable material, the location of the permeable or semi-permeable material may be situated so as to deliver the substance at a particular location once the device is implanted in the eye.

In another embodiment, the body member 2 is fabricated of a synthetic biodegradable polymer containing microparticles of the substance to be delivered. Thus, in this embodiment, as the polymer decomposes, the substance to be delivered is released into the eye. Release time is a function of the polymer and the shape and size of the body member 2 and may be readily determined by one of ordinary skill in the art. Such biodegradable polymers may vary depending on the particular application and may be readily determined by one of skill in the art. By way of example, some suitable biodegradable polymers may include polyesters of molecular weight from about 4,000 to about 100,000, homopolymers and copolymers of polylactic acid and polyglycolic acid, polycaprolactone, homopolymers and copolymers of polyanhydrides such as terephthalic acid anhydride, bis(p-anhydride) and poly(p-carboxyphenoxy) alkyl, homopolymers and copolymers of dicarboxylic acids such as sebacic, adipic, oxalic, phthalic and maleic acid, polymeric fatty acid dimer compounds such as polydodecanedioic acid polyorthoesters, poly(alkyl-2-cyanoacrylate) such as poly(hexyl-2-cyanoacrylate), collagen (gelatin), polyacetals, divinyloxyalkylenes, polydihydropyrans, polyphosphazenes, homopolymers and copolymers of amino acids such as copolymers of leucine and methyl glutamate, polydioxinones, polyalkylcyano acetates, polysaccharides and their derivatives such as dextran and cyclodextran, cellulose and hydroxymethyl cellulose.

In another embodiment, rather than a single lumen 10, the non-linear body member 2 includes a plurality of lumens 10a capable of housing and delivering a plurality of substances. Thus, for example, each lumen 10a may be in fluid communication with plurality of ports 12a. These ports 12a are similar to the single port 12 described above. (e.g. the ports 12a may include a cover that may be removed for injection of the substance and replaced when the substance has been injected, or the ports 12a may be fabricated of an injectable self-sealing material) If desired, the lumens 10a and ports 12a may be arranged such that each lumen 10a may be filled with a different substance through the corresponding ports 12a. Thus, the single device may be used to deliver more than one substance if desired.

Figure 4A:
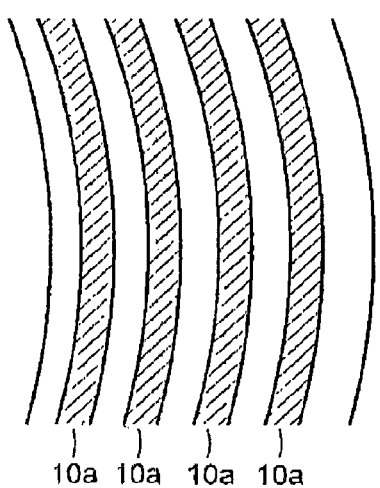
FIG. 4a is an enlarged view of a portion of the body member of the delivery device in accordance with another embodiment of the present invention showing a plurality of lumen.
Figures 1, 4B:
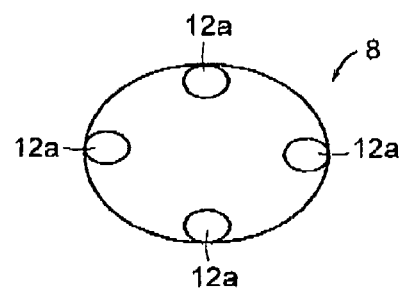
FIG. 1 illustrates transcleral placement of the delivery device in accordance with one embodiment of the present invention.
FIG. 4b is an exploded view of the cap or rim and a portion of the body member shown in FIG. 4a showing one arrangement of a plurality of lumens.
Figure 4B:
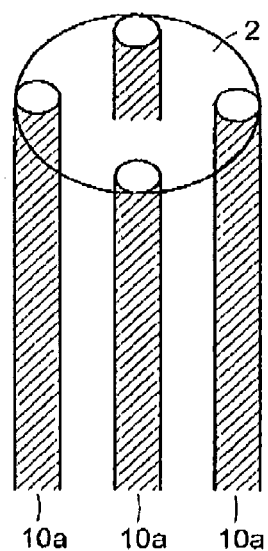

In one embodiment, the plurality of lumens 10a are situated in a ring about the outer circumference of the body member 2 as shown in FIG. 4b. The substance(s) may be injected into the lumens 10a for delivery through a delivery mechanism, which may be any of the delivery mechanisms described above or a combination of the delivery mechanisms described above.

Figures 1, 4C:
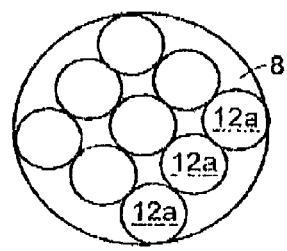

In another embodiment, a plurality of lumen 10a are clustered within the body member 2 as shown in FIG. 4c. The substance(s) may be injected into the lumens 10a for delivery through a delivery mechanism. In this embodiment, the inner lumens 10a preferably deliver their housed substances through one or more apertures 16, 16a located near the distal end 6 of the body member 2, while the outer lumens 10a located at the outer circumference of the body member 2 may deliver their housed substances through one or more apertures 16, 16a located near the distal end 6 of the body member 2, a plurality of openings 18 along the body member 2, and/or through the material forming the body member 2 as described above.

Figures 1, 4D:
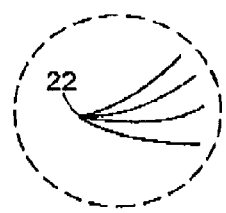
FIG. 4d illustrates a magnified view of a portion of a body member in accordance with another embodiment, wherein the body member comprises a cluster of tubes.
Figures 2, 4D:
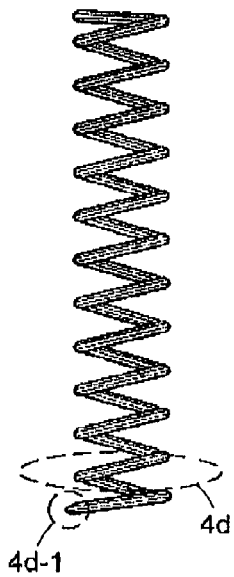
Figure 4C:
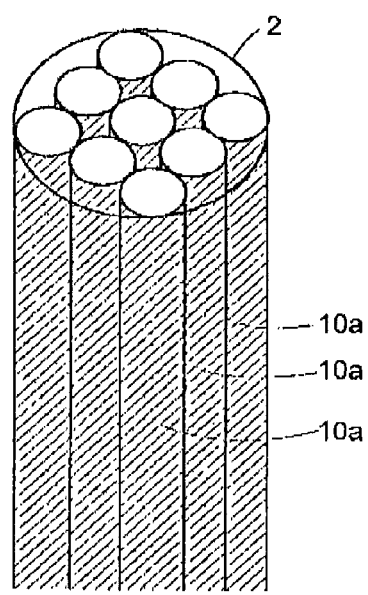
Figure 4D:
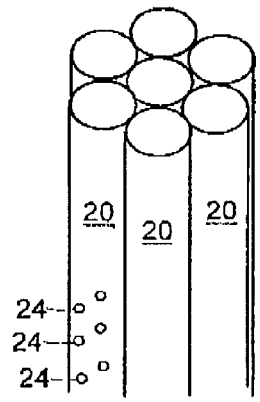

In yet another embodiment, the non-linear body member 2 is formed of a plurality of tubes 20 clustered and wound into a coil shape as shown in FIG. 4d. In this embodiment, the substance(s) to be delivered is/are inserted into and housed within the plurality of hollow tubes 20. The plurality of tubes 20 may contain different substances or the same substance as desired. The substances are then delivered by one or more of the delivery mechanisms set out above. For example, in one embodiment, one or more of the tubes 20 may have one or more exit apertures 22 at their distal ends through which the substance(s) can be delivered. One or more tubes 20 may also have a plurality of openings 24 along their lengths through which the substance(s) can be delivered. Still further, one or more tubes 20 can be fabricated of a material permeable or semi-permeable to the substance contained within the tubes 20. Thus, it is possible for each tube 20 to have one or more of the various types of delivery mechanisms and, also, it is possible to for different tubes to have different types of delivery mechanisms. In this way, each tube 20 can be designed to provide the optimal type of delivery based on the substance to be delivered, the location of delivery and the desired rate of delivery.

Figure 5A:
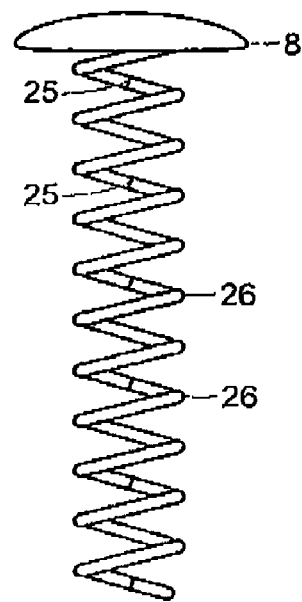
FIG. 5a illustrates the delivery device in accordance with another embodiment of the present invention showing a lumen separated into a plurality of compartments.
Figure 5B:
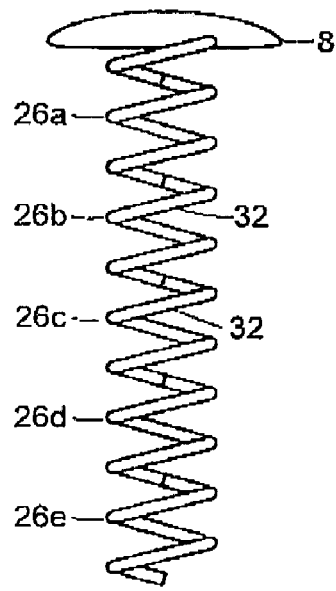
FIG. 5b shows the delivery device of FIG. 5a and further shows one type of delivery mechanism in accordance with the present invention.
Figure 5C:
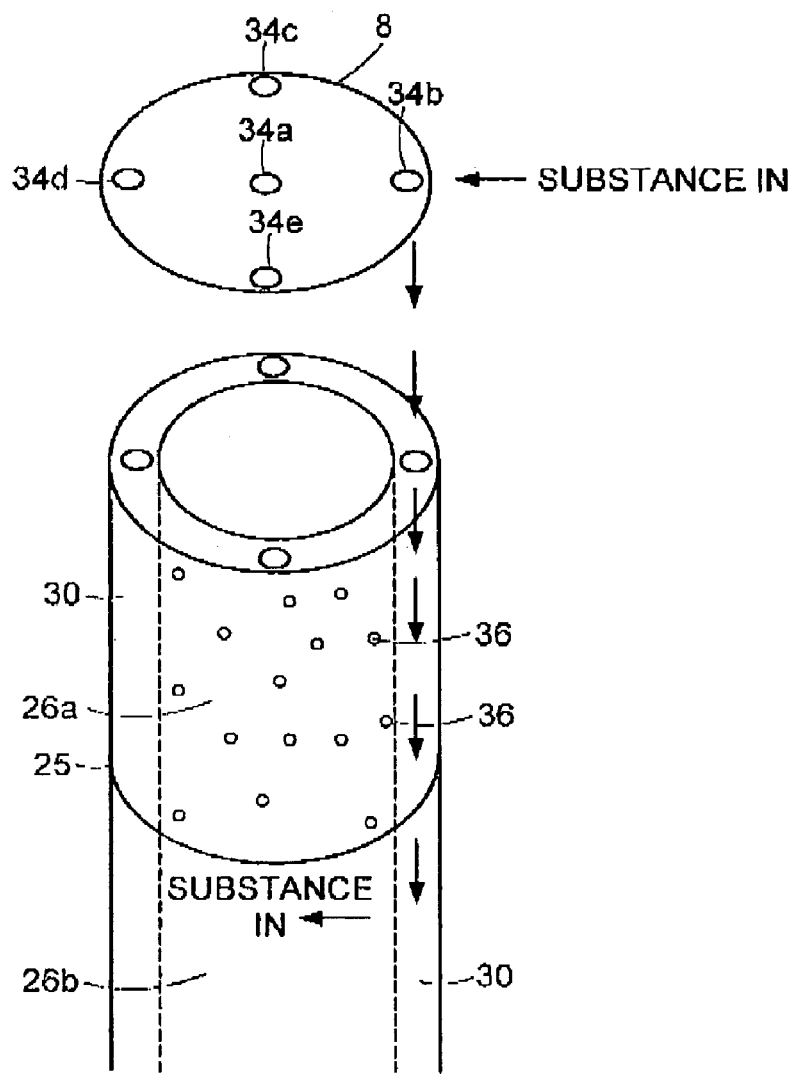
FIG. 5c shows an exploded view of a segment of the device delivery mechanism shown in FIG. 5b, wherein conduits are located within the wall of the body member along its circumference.

In another embodiment, a plurality of substances may be delivered by a single device by providing a body member 2 with a lumen 10 having impermeable dividers 25 located along the length of the lumen 10 as shown for example, in FIG. 5a. Thus, the lumen 10 would contain a plurality of compartments 26, each of which could be filled with a different substance. These compartments 26 could be filled prior to insertion through an injection port 32 located, for example, in the side of each compartment 16 as shown in FIG. 5b. In another embodiment, the device may be filled after it is implanted by providing a plurality of conduits 30 each in fluid communication with a corresponding compartment 25. These conduits 30 may be located within the wall of the body member 2, along the circumference of the body member 2, for example, as shown in FIG. 5c. The substances could then be injected through a plurality of ports 34a, 34b, 34c, 34d, 34e each in fluid communication with a corresponding conduit 30. Thus, a substance could be injected into the first compartment 26a just below the rim or cap 8 by a port 34a in the center of the rim or cap 8, which delivers the substance directly into the first compartment 26a. A substance injected into the second port 36b, would flow through conduit 30 and would flow through an aperture in the wall of the body member 2 into second compartment 26b, and so on.

The substance injected into each of the compartments 26a, 26b, 26c, 26d, 26e, is then delivered to the eye by a delivery mechanism, which may be one or more of the delivery mechanisms described above. For example, substance in compartment 26a may be delivered through one or more apertures 36 in the walls of the compartment 26a. Compartment 26b could be fabricated of a material that is permeable or semi-permeable to the substance in the compartment 26b such that substance in compartment 26b may be delivered by diffusion through the walls of the compartment. Such materials are set out above and may be readily determined by those in skill in the art depending on the substance in the compartment to be delivered and the desired rate of delivery of the substance. Substance in compartment 26e, located at the end of the non-linear body member 2 could be delivered by an exit port (not shown) located at the distal end of the compartment 26e and, also, could be delivered by a plurality of apertures (not shown) in the walls of the compartment 26e. In this way, each compartment may be designed for optimal delivery the particular substance housed within the compartment.

In another embodiment, each compartment 26a, 26b, 26c, 26d, 26e is designed for selective "opening" or activation by a laser (via heat or photodisruption). For example, a laser could be used to create apertures in the walls of the desired compartment 26a, 26b, 26c, 26d or 26e when the particular substance is to be delivered. As such, release of each substance could be controlled upon demand by a physician.

In yet another embodiment, a pump-driven (e.g. Spring, gas-driven, nitinol, piezoelectric, osmotic) system (not shown) including is coupled to the device, allowing for more sustained delivery. In this embodiment, the one or more lumens 10, 10a can be refilled by injection into the lumen(s) 10, 10a themselves or through an external conduit. For example, a separate pump device and reservoir housing one or more substances (not shown) could be located within the eye or remotely (i.e. behind the ear subcutaneously). If the pump and reservoir are located behind the ear, a conduit between the pump and the delivery device within the eye could run subcutaneously into the orbit, subconjunctively and through the sclera into the posterior chamber. The conduit must have sufficient slack to allow for ocular movements without displacing the conduit.

For added structural support, the delivery device may further include a nonbiodegradable backbone (not shown) located along the non-linear body member 2. For example, in one embodiment, one or more thin, wire-like members fabricated of a nonbiodegradable material, may be located within the walls of the body member 2 or, for example, in the center of the cluster of tubes 20 shown in FIG. 4d. Such nonbiodegradable materials are well-known and may be readily determined by one of skill in the art. By way of example, some suitable nonbiodegradable polymers may include, for example, polymethylmethacrylate, a silicone elastomer, or silicone rubber. Other suitable non-erodible, biocompatible polymers which may be used in fabricating the body member 2 may include polyolefins such as polypropylene and polyethylene, homopolymers, and copolymers of vinyl acetate such as ethylene vinyl acetate copolymer, polyvinylchlorides, homopolymers and copolymers of acrylates such as polyethylmethacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, natural rubber, polyisobutylene, polymethylstyrene and other similar non-erodible biocompatible polymers.

In another embodiment, the delivery device 1 includes backbone (not shown) fabricated of a shape memory material described above. In this embodiment, for example, the body member 2 may be fabricated of any of the materials described above. In one embodiment, for example, the body member 2 is fabricated of a flexible material and a shape memory backbone located within the wall of the body member 2 or, for example, in the center of a cluster of tubes 20 shown in FIG. 4d. Thus, the backbone, along with the body portion of the device, is first deformed to a shape that makes it easier to insert into the eye, such as a linear shape. The backbone will hold the device in this deformed shape. After the device is inserted into the eye, the backbone, along with the body portion of the device, will then return to the remembered shape.

The dimensions of the delivery device will depend on the intended application of the device, and will be readily apparent to those having ordinary skill in the art. By way of example, when the delivery device is used to deliver substances to the posterior chamber of the eye, the device is preferably designed for insertion through a small incision that requires few of no sutures for scleral closure at the conclusion of the procedure. As such, the device is preferably inserted through an incision that is no more than about 1 mm in cross-section, e.g. ranging from about 0.25 mm to about 1 mm in diameter, more preferably less than 0.5 mm in diameter. As such, the cross-section of the tube forming the body member 2, or the cluster of tubes 20 as shown in FIG. 4d, is preferably no more than about 1 mm, e.g. preferably ranging from about 0.25 mm to about 1 mm in diameter, and, more preferably, is no greater than 0.5 mm. If the tube forming the body member 2 is not cylindrical, the largest dimension of the cross section can be used to approximate the diameter for this purpose. When used to deliver agents to the posterior chamber of the eye, the body member 2 preferably has a length from its proximal end 4 to its distal end 6 that is less than about 1.5 cm, e.g. ranges from about 0.5 cm to about 1.5 cm such that when the rib or cap 8 abuts the outer surface of the eye, the delivery mechanism is positioned near the posterior chamber of the eye.

The use of the delivery device of the present invention can be further understood from the following discussion relating to a method for treating chronic diseases of the eye by sustained release of therapeutic agent to the eye and with reference to FIGS. 1-6.

The delivery device is generally used by the following procedure: the delivery device is prepared, either empty or housing the substance to be delivered.

Figure 6:
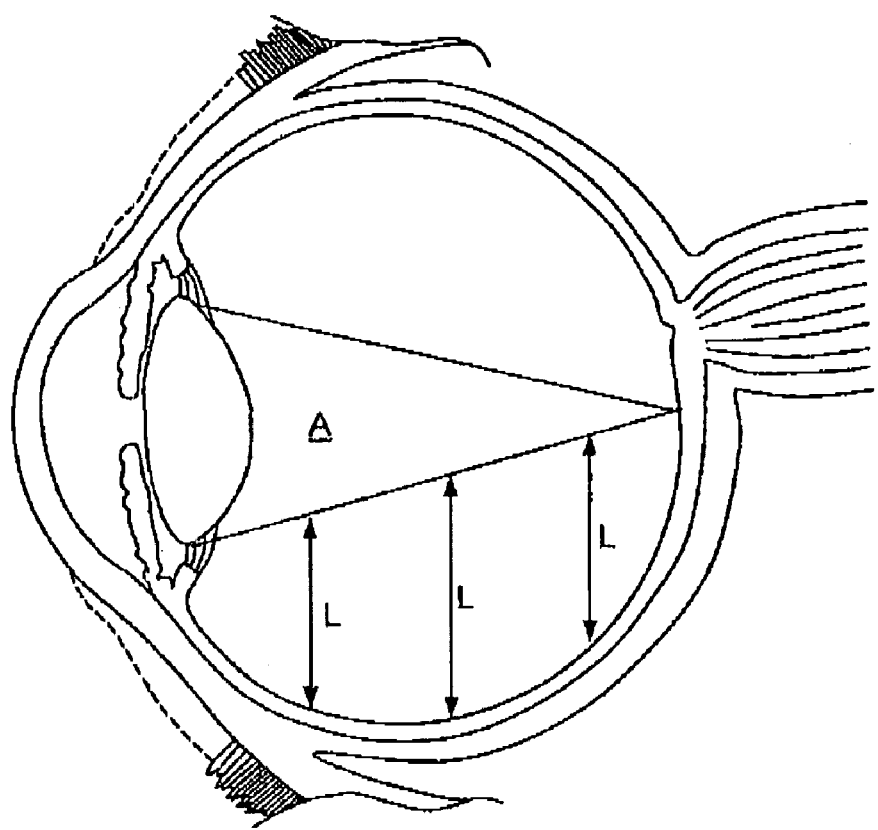
FIG. 6 shows a shows a cross-sectional view of an eye illustrating the central visual field of the eye.
Figure 7:
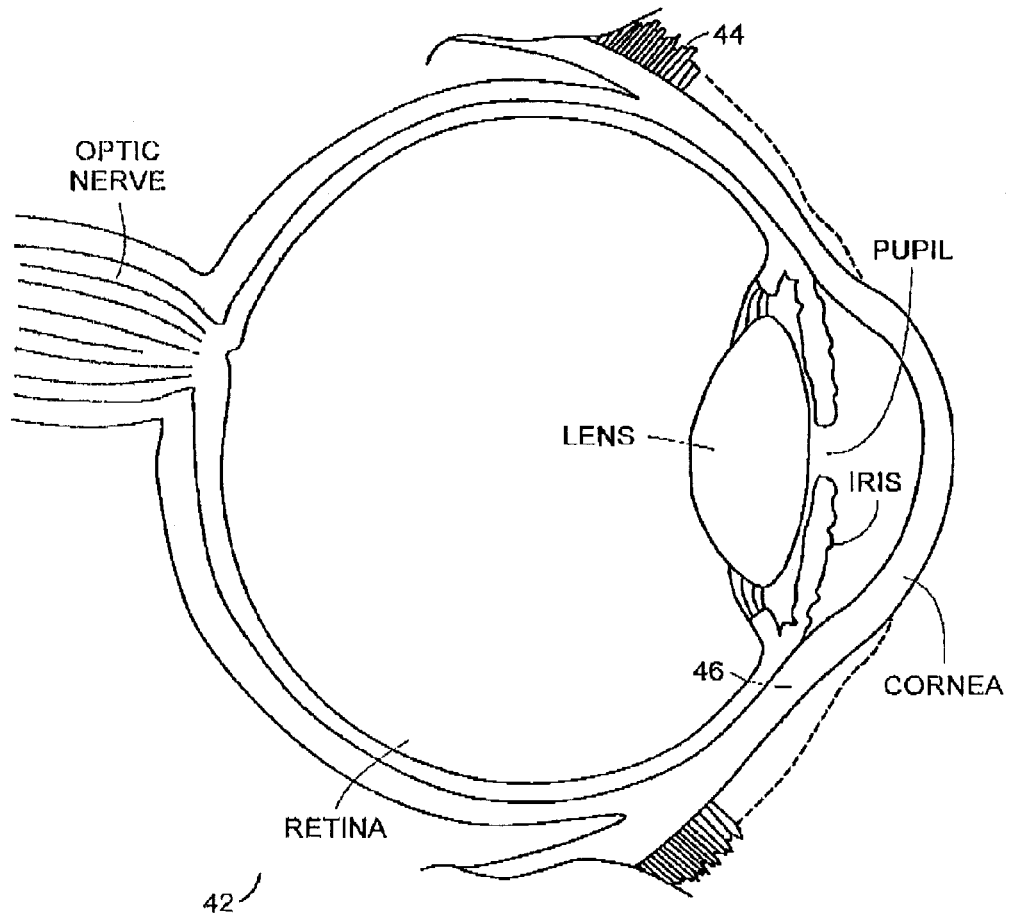
FIG. 7 shows a cross-sectional schematic view of an eye illustrating one technique of pulling back of the conjunctiva to provide access into the eye for insertion of the delivery device of the present invention.

In one embodiment, an incision is made to provide access to the treatment site. For example, when used to deliver therapeutic agent to the posterior chamber of the eye, a sclerotomy is created for insertion of the delivery device. Conventional techniques may be used for the creation of the sclerotomy. Such techniques require the dissection of the conjunctiva 44 and the creation of pars plana scleral incisions through the sclera 46. As shown in FIG. 6, the dissection of the conjunctiva 44 typically involves pulling back the conjunctiva 44 about the eye 42 so as to expose large areas of the sclera 46 and the clipping or securing of the conjunctiva 44 in that pulled back state (normal position of conjunctiva shown in phantom). In other words, the sclera 46 is not exposed only in the areas where the pars plana scleral incisions are to be made. Surgical instruments used in the procedure are then passed through these incisions. Thus, the incisions created for the procedure must be made large enough to accommodate the instruments required for the procedure. Alternatively, during this procedure, rather than making an incision through which the device is inserted, the distal end 6 may be pointed or beveled and used to create the incision.

Alternatively, the creation of the sclerotomy may be accomplished by use of an alignment device and method, such as that described in U.S. Ser. No. 09/523,767, the teachings of which are incorporated herein by reference, that enables sutureless surgical methods and devices therefore. In particular, such methods and devices do not require the use of sutures to seal the openings through which instruments are inserted. The alignment devices are inserted through the conjunctiva and sclera to form one or more entry apertures. Preferably, the alignment devices are metal or polyimide cannulas through which the surgical instruments used in the procedure are inserted into the eye.

The body member 2 is then inserted into the eye. For example, in embodiments wherein the body member 2 has a coiled shape, the body member 2 is inserted into the eye by screwing or twisting the body member 2 into eye until the rim or cap 8 abuts the outer surface of the eye. In embodiments wherein the body member 2 or a backbone of the body member is fabricated of a shape memory material, the shape memory material is first cooled to a temperature at which the martensite phase is stable and the device is deformed, for example, into a linear shape. The device is then inserted into the eye. To return the device to its memory shape, the device is left unrestrained and is simply heated to a temperature above the martensite phase temperature. For example, the shape memory material may be heated by a laser to return the device to a temperature above the martensite phase temperature. The shape memory material may also be selected such that the martensite phase temperature is below body temperature so that the material is simply cooled to below body temperature, deformed to a linear shape and inserted into the eye. Then, as the material warms up within the eye to body temperature, the device returns to its remembered shape.

After the device is inserted into the eye, the rim or cap 8 may then be sutured or otherwise secured to the sclera to hold the delivery device in place. If a cover is used to close the port(s) 12, 12a it is removed at this time, and, if used, a collar for providing a snug fit about the syringe or other injection mechanism is mounted on the port(s) 12, 12a. The syringe or other injection mechanism is then connected to the port(s) 12, 12a for injection of the one ore more substances into the delivery device. If the port(s) 12, 12a are composed of an injectable self-sealing material through which the needle of a syringe or other injection mechanism may be inserted and which seals off automatically when the needle other injection mechanism is removed, the needle or other injection mechanism is simply inserted through the port and the substance injected. Following injection, the conjunctiva may be adjusted to cover the rim or cap 8 of the device.

When the device is used to deliver agents to the eye for the treatment of a variety of ocular conditions such as, for example, retinal detachment, occlusions, proliferative retinopathy, diabetic retinopathy, inflammations such as uveitis, choroiditis and retinitis, degenerative disease, vascular diseases and various tumors including neoplasms, some substances suitable for delivery to the eye may include, for example, antibiotics such as tetracycline, chlortetracycline, bacitracin, neomycin, polymyxin, gramicidin, cephalexin, oxytetracycline, chloramphenicol, rifampicin, ciprofloxacin, tobramycin, gentamycin, and erythromycin and penicillin; antifungals such as amphotericin B and miconazole; antibacterials such as sulfonamides, sulfadiazine, sulfacetamide, sulfamethizole and sulfisoxazole, nitrofurazone and sodium propionate; antivirals, such as idoxuridine trifluorotymidine, acyclovir, ganciclovir and interferon; antibacterial agents such as nitrofurazone and sodium propionate; antiallergenics such as sodium cromoglycate, antazoline, methapyriline, chlorpheniramine, cetirizine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate; fluoromethalone, betamethasone and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; decongestants such as phenylephrine, naphazo line, and tetrahydrazoline; miotics and anti-cholinesterase such as pilocarpine, salicylate, carbachol, acetylcholine chloride, physostigmine, eserine, diisopropyl fluorophosphate, pholpholine iodine, and demecarium bromide; mydriatics such as atropine sulfate, cyclopentolate, homatropine, scopolamine, tropicamide, eucatropine, and hydroxyamphetamine; sympathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol HCl and betaxolol HCl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamnide; inhibitors of angiogenesis such as angiostatin, anecortave acetate, thrombospondin, and anti-VEGF antibody; and other therapeutic agents such as prostaglandins, antiprostaglandins and prostaglandin precursors.

In some applications, additives may further be included in the substance and, for example, some suitable additives may include water, saline, dextrose, carriers, preservatives, stabilizing agents, wetting agents, emulsifying agents or other similar materials.

Once the therapeutic agent had been delivered to the treatment area, the delivery device may be refilled for further delivery or removed if the required dose of agent has been delivered for treatment of the condition.

The invention is not be limited to ocular applications, and is particularly useful in other limited access regions such as the inner ear.

The present invention also includes kits that comprise one or more devices of the invention, preferably packaged in sterile condition. Kits of the invention also may include, for example, one or more body members 2, means for suturing or securing the device to the sclera, etc. for use with the device, preferably packaged in sterile condition, and/or written instructions for use of the device and other components of the kit.

All documents mentioned herein are incorporated by reference herein in their entirety.

The foregoing description of the invention is merely illustrative thereof, and it is understood that variations and modifications can be effected without departing from the scope or spirit of the invention as set forth in the following claims.

What is claimed is:

1. An implantable ocular drug delivery device comprising:
   a non linear shaped body member having a proximal end and a distal end, the body member comprising a tube provided in a coil or zig-zag shape along its entire length from its proximal end to its distal end, and that is implanted within a patient eye to deliver a drug substance to the patient eye via the body member; and
   a cap element at the proximal end of the body member sized to provide a cross-section larger than the cross-section of the coil or zig-zag shape, wherein the body member is positioned within the vitreous fluid and the cap element abuts an incision through which the device is inserted to stabilize the device once implanted, wherein the device is insertable through an incision approximately the same size as the outer diameter of the tube forming the body member.

2. The device of claim 1 wherein the device body member comprises at least three deviations from a linear path.

3. The device of claim 1 wherein the device body member comprises at least four deviations from a linear path.

4. The device of claim 1 wherein the device body member comprises at least five deviations from a linear path.

5. The device of claim 1 wherein the device body member comprises a helical shape.

6. The device of claim 1 wherein the device body member comprises a substantially Z-shape.

7. The device of claim 1 wherein the cap element is in contact with a patient eye outer surface while the body member is inserted into the eye.

8. The device of claim 1 wherein the device comprises a therapeutic agent for delivery to the patient during use of the device.

9. The device of claim 1 wherein the device body member comprises a polymer.

10. The device of claim 1 wherein the device body member comprises a polymer that comprises a therapeutic substance to be delivered to the patient eye.

11. An implantable ocular drug delivery device comprising:
    a coil-shaped body member comprising a tube wound into a coil shape that is implanted within a patient eye to deliver a drug substance to the patient eye via the body member; and
    a cap element sized to provide a cross-section larger than the cross-section of the coil-shaped body member, wherein the body member is positioned within the vitreous fluid and the cap element abuts an incision through which the device is inserted to stabilize the device once implanted, wherein the device is insertable through an incision approximately the same size as the outer diameter of the tube forming the body member.

12. The device of claim 11 wherein the device comprises a therapeutic agent for delivery to the patient during use of the device.

13. The device of claim 11 wherein the device body member comprises a polymer.

14. The device of claim 11 wherein the device body member comprises a polymer that comprises a therapeutic substance to be delivered to the patient.

15. A method for treating a patient comprising:
    (a) providing a delivery device comprising a non-linear shaped body member comprising a tube provided in a coil or zig-zag shape, the body member having a proximal end and a distal end, and a cap element at the proximal end, the cap element sized to provide a cross-section larger than the cross-section of the coil or zig-zag shape;
    (b) inserting the device into a patient's eye through an incision, the incision being approximately the same size as the outer diameter of the tube forming the body member, whereby the body member resides in the vitreous fluid of the patient's eye and the cap element remains outside the incision through which the device is inserted and abuts the outer surface of the eye to stabilize the device; and
    (c) allowing a therapeutic substance to be administered to the patient via the body member.

16. The method of claim 15 wherein the device body member comprises at least three deviations from a linear path.

17. The method of claim 15 wherein the device body member comprises at least four deviations from a linear path.

18. The method of claim 15 wherein the device body member comprises at least five deviations from a linear path.

19. The method of claim 15 wherein the device body member comprises a helical shape.

20. The method of claim 15 wherein the device body member comprises a substantially Z-shape.

21. The method of claim 15 wherein the substance administered to the patient is chosen from one or more of an antibiotic, an antifungal, an antiviral, an antibacterial, an antiallergenic, an anti-inflammatory, a decongestant, a miotic or anti-cholinesterase, a mydriatic, a sympathomimetic, an antineoplastic, a hormonal agent, a beta adrenergic blocker, a growth factor, a carbonic anhydrase inhibitor, an angiogenesis inhibitor, a prostaglandin or an antiprostaglandin.

22. The method of claim 15 wherein the device body member comprises a polymer.

23. The method of claim 15 wherein the device body member comprises a polymer that comprises a therapeutic substance to be delivered to the patient.

24. The method of claim 15 wherein the device comprises a shape memory material.

25. A method for treating a patient comprising:
    (a) providing a drug delivery device comprising a coil-shaped body member and a cap element sized to provide a cross-section larger than the cross-section of the coil-shaped body member;
    (b) inserting into a patient eye the device whereby the coil-shaped body member is placed in the vitreous fluid of the patient eye and the cap element remains outside the eye and abuts the incision, wherein the device is inserted through an incision smaller than the cross-section of the coil-shaped body member; and
    (c) allowing a substance to be delivered by the device to the patient.

26. The method of claim 25 wherein the substance delivered to the patient eye is chosen from one or more of an antibiotic, an antifungal, an antiviral, an antibacterial, an antiallergenic, an anti-inflammatory, a decongestant, a miotic or anti-cholinesterase, a mydriatic, a sympathomimetic, an antineoplastic, a hormonal agent, a beta adrenergic blocker, a growth factor, a carbonic anhydrase inhibitor, an angiogenesis inhibitor, a prostaglandin or an antiprostaglandin.

27. The method of claim 25 wherein the device body member comprises a polymer.

28. The method of claim 25 wherein the device body member comprises a polymer that comprises a therapeutic substance to be delivered to the patient eye.

29. The method of claim 25 wherein the device comprises a cap element that is in contact with the patient eye outer surface while the body member is inserted into the eye.

30. The method of claim 25 wherein the device comprises a shape memory material.

31. A method for treating a patient comprising:
(a) providing a drug delivery device comprising a non-linear shaped body member having a coil or zig-zag shape, and a cap element sized to provide a cross-section larger than the coil or zig-zag shape;
(b) inserting into a patient eye the device whereby the body member resides in the vitreous fluid of the patient eye and the cap element remains outside the eye and abuts the incision, wherein the incision is smaller than the cross-section of the coil or zig-zag shaped body member; and
(c) administering a substance to the patient via the body member.

32. The method of claim 31 wherein the device body member comprises at least three deviations from a linear path.

33. The method of claim 31 wherein the device body member comprises at least four deviations from a linear path.

34. The method of claim 31 wherein the device body member comprises at least five deviations from a linear path.

35. The method of claim 31 wherein the device body member comprises a helical shape.

36. The method of claim 31 wherein the device body member comprises a substantially Z-shape.

37. The method of claim 36 wherein the substance administered to the patient eye is chosen from one or more of an antibiotic, an antifungal, an antiviral, an antibacterial, anti-allergenic, an anti-inflammatory, a decongestant, a miotic or anti-cholinesterase, a mydriatic, a sympathomimetic, an anti-neoplastic, a hormonal agent, a beta adrenergic blocker, a growth factor, a carbonic anhydrase inhibitor, an angiogenesis inhibitor, a prostaglandin or an antiprostaglandin.

38. The method of claim 31 wherein the device body member comprises a polymer.

39. The method of claim 31 wherein the device body member comprises a polymer that comprises a therapeutic substance to be delivered to the patient eye.

40. The method of claim 31 wherein the device is inserted until the cap element is in contact with the outer surface of the patient eye.

41. The method of claim 15, 25, or 31 wherein the device is inserted by twisting or screwing the device into the eye.

42. The method of claim 31 wherein the device comprises a shape memory material.

43. The method of claim 15, 25, or 31, wherein the incision comprises a sclerotomy.

44. The method of claim 15, 25, or 31, wherein the device is implanted in a minimally invasive surgical procedure.

45. The method of claim 15, 25, or 31, wherein the device is implanted at the pars plana.

46. An implantable ocular drug delivery device comprising:
a) a coil-shaped body member that is implanted within the vitreous fluid of a patient eye during use of the device to deliver a drug substance to the patient eye, the body member comprising a tube wound into a coil shape;
b) a cap element sized to provide a cross-section larger than the cross-section of the coil-shaped body member, wherein the cap element is in contact with the patient eye outer surface while the body member is inserted within the eye; wherein the device is insertable within the eye through an incision approximately the same size as the outer diameter of the tube forming the body member.

47. The device of claim 46 wherein the device comprises a therapeutic agent for delivery to the patient eye during use of the device.

48. The device of claim 46 wherein the cap element mates the body member at a proximal end of the device.

49. The device of claim 46 wherein the device body member comprises a polymer.

50. The device of claim 46 wherein the device body member comprises a polymer that comprises a therapeutic substance to be delivered to the patient eye.

51. The device of claim 46 wherein the tube has a cross-section of 0.5 mm or less in diameter.

52. The device of claim 51 wherein the tube has a circular cross-section in the range of 0.25 to 0.5 mm in diameter.

53. The device of claim 46 wherein the drug substance is injected into the body member through a port in a center of the cap element.

54. An implantable ocular drug delivery device comprising:
a non-linear shaped body member that has a coil or zig-zag shape and that is implanted within a patient eye during use of the device to deliver a drug substance to the patient eye via the body member; and
a cap element sized to provide a cross-section larger than the cross-section of the coil or zig-zag shape, the cap element configured to be in contact with the patient eye outer surface while the body member is inserted to the eye;
wherein the device is implantable within the vitreous fluid of a patient eye through an incision smaller than the cross-section of the coil or zig-zag shaped body member.

55. The device of claim 1, 11, 46, or 54, wherein at least a portion of the body member comprises a biodegradable polymer.

56. The device of claim 55, wherein the biodegradable polymer contains microparticles of the drug substance, wherein as the polymer degrades, the drug substance is released.

57. The device of claim 55, wherein the biodegradable polymer is selected from polyesters of molecular weight of 4,000 to 100,000, homopolymers and copolymers of polylactic acid and polyglycolic acid, polycaprolactone, homopolymers and copolymers of polyanhydrides, homopolymers and copolymers of dicarboxylic acids, polymeric fatty acid dimer compounds, poly(alky-2-cyanoacrylate), poly(hexyl-2-cyanoacrylate), collagen (gelatin), polyacetals, divinyloxyalkylenes, polydihydropyrans, polyphosphazenes, homopolymers and copolymers of amino acids, polydioxinones, polyalkylcyano acetates, polysaccharides and their derivatives, and cellulose and hydroxymethyl cellulose.

58. The device of claim 55, wherein the biodegradable polymer comprises one or more of terephthalic acid anhydride, bis(p-anhydride), poly(p-carboxyphenoxy) alkyl, sebacic acid, adipic acid, oxalic acid, phthalic acid, maleic acid, polydodecanedioic acid polyorthoesters, copolymers of leucine and methyl glutamate, dextran, or cyclodextran.

59. The device of claim 1, 11, 46, or 54, wherein at least a portion of the device comprises a material that is permeable or semi-permeable to the drug substance.

60. The device of claim 59, wherein the portion of the device that comprises a permeable or semi-permeable material represents a percentage of the overall body member material, and wherein the percentage of body member material composed of permeable or semi-permeable material controls rate of delivery of the drug substance.

61. An implantable ocular drug delivery device comprising:

a coil-shaped body member comprising a tube provided in a coil shape that is implanted within the vitreous fluid of a patient eye to deliver a drug substance to the patient via the body member; and a cap element sized to provide a cross-section larger than the cross-section of the coil-shaped body member, the cap element being in contact with the coil-shaped body member;

wherein the device is insertable through an incision approximately the same size as the outer diameter of the tube forming the body member.

62. The device of claim 61, wherein at least a portion of the body member comprises a biodegradable polymer.

63. The device of claim 62, wherein the biodegradable polymer contains microparticles of the drug substance, wherein as the polymer degrades, the drug substance is released.

64. The device of claim 62, wherein the biodegradable polymer is selected from polyesters of molecular weight of 4,000 to 100,000, homopolymers and copolymers of polylactic acid and polyglycolic acid, polycaprolactone, homopolymers and copolymers of polyanhydrides, homopolymers and copolymers of dicarboxylic acids, polymeric fatty acid dimer compounds, poly(alky-2-cyanoacrylate), poly(hexyl-2-cyanoacrylate), collagen (gelatin), polyacetals, divinyloxyalkylenes, polydihydropyrans, polyphosphazenes, homopolymers and copolymers of amino acids, polydioxinones, polyalkylcyano acetates, polysaccharides and their derivatives, and cellulose and hydroxymethyl cellulose.

65. The device of claim 62, wherein the biodegradable polymer comprises one or more of terephthalic acid anhydride, bis(p-anhydride), poly(p-carboxyphenoxy) alkyl, sebacic acid, adipic acid, oxalic acid, phthalic acid, maleic acid, polydodecanedioic acid polyorthoesters, copolymers of leucine and methyl glutamate, dextran, or cyclodextran.

66. The device of claim 1, 11, 46, 54, or 61, wherein at least a portion of the device comprises a material that is permeable or semi-permeable to the drug substance.

67. The device of claim 66, wherein the portion of the device that comprises a permeable or semi-permeable material represents a percentage of the overall body member material, and wherein the percentage of body member material composed of permeable or semi-permeable material controls rate of delivery of the drug substance.

68. The device of claim 1, 46, or 61 wherein the tube has a circular cross-section.

* * * * *